US012702758B2

(12) United States Patent
Lindholm

(10) Patent No.: US 12,702,758 B2
(45) Date of Patent: Aug. 11, 2026

(54) TORSION SPRING MECHANISM FOR MEDICAMENT DELIVERY DEVICE, AND MEDICAMENT DELIVERY DEVICE COMPRISING SAID MECHANISM

(71) Applicant: SHL MEDICAL AG, Zug (CH)

(72) Inventor: Joakim Lindholm, Saltsjo-Boo (SE)

(73) Assignee: SHL Medical AG, Zug (CH)

( * ) Notice: Subject to any disclaimer, the term of this patent is extended or adjusted under 35 U.S.C. 154(b) by 647 days.

(21) Appl. No.: 18/035,994

(22) PCT Filed: Nov. 15, 2021

(86) PCT No.: PCT/EP2021/081635
§ 371 (c)(1),
(2) Date: May 9, 2023

(87) PCT Pub. No.: WO2022/106333
PCT Pub. Date: May 27, 2022

(65) Prior Publication Data

US 2023/0405228 A1 Dec. 21, 2023

(30) Foreign Application Priority Data

Nov. 20, 2020 (EP) .................................... 20208887

(51) Int. Cl.
*A61M 5/20* (2006.01)
*A61M 5/315* (2006.01)

(52) U.S. Cl.
CPC ...... *A61M 5/2033* (2013.01); *A61M 5/31583* (2013.01); *A61M 2005/2013* (2013.01); *A61M 2005/202* (2013.01)

(58) Field of Classification Search
CPC ............ A61M 5/2033; A61M 5/31583; A61M 2005/202; A61M 2005/2013
See application file for complete search history.

(56) References Cited

U.S. PATENT DOCUMENTS

2015/0246181 A1 9/2015 Fourt
2017/0119973 A1* 5/2017 Roervig ................. A61M 5/20
(Continued)

FOREIGN PATENT DOCUMENTS

CN 105120926 A 12/2015
CN 105492048 A 4/2016
(Continued)

OTHER PUBLICATIONS

International Search Report and Written Opinion for Int. App. No. PCT/EP2021/081635, mailed Feb. 8, 2022.

*Primary Examiner* — Tasnim Mehjabin Ahmed
(74) *Attorney, Agent, or Firm* — McDonnell Boehnen Hulbert & Berghoff LLP

(57) ABSTRACT

A mechanism having a base structure; a plunger rod movable along a longitudinal axis; a driver rotatable about the longitudinal axis and engaging the plunger rod; a torsion spring connected to the driver and to the base structure, the torsion spring being arranged to rotationally drive the driver; and at least one support part arranged to support the torsion spring in a lateral direction; wherein the mechanism has at least one rotational interface between the driver and the base structure; and wherein the at least one rotational interface is positioned at between 0.5% and 99.5% of a length of the torsion spring; and/or wherein the at least one rotational interface has a first rotational interface positioned at less than 10% of the length of the torsion spring and a second rotational interface positioned at more than 90% of the length of the torsion spring.

20 Claims, 8 Drawing Sheets

(56) References Cited

U.S. PATENT DOCUMENTS

| | | | |
|---|---|---|---|
| 2017/0246395 A1 | 8/2017 | Daniel | |
| 2019/0046734 A1 | 2/2019 | Jakobsen et al. | |
| 2019/0275254 A1 * | 9/2019 | Klitmose .......... | A61M 5/31553 |
| 2019/0328969 A1 | 10/2019 | Marsh | |

FOREIGN PATENT DOCUMENTS

| | | | |
|---|---|---|---|
| CN | 205618492 | U | 10/2016 |
| CN | 104703643 | A | 9/2018 |
| CN | 108952536 | A | 12/2018 |
| CN | 110410415 | A | 11/2019 |
| CN | 106456888 | A | 12/2019 |
| CN | 110585028 | A | 12/2019 |
| EP | 2986334 | B1 | 3/2019 |
| WO | 2015048961 | A2 | 4/2015 |
| WO | 2017/085090 | A1 | 5/2017 |
| WO | 2017109713 | A1 | 6/2017 |
| WO | 2018/100126 | A1 | 6/2018 |
| WO | 2019/002020 | A1 | 1/2019 |

* cited by examiner

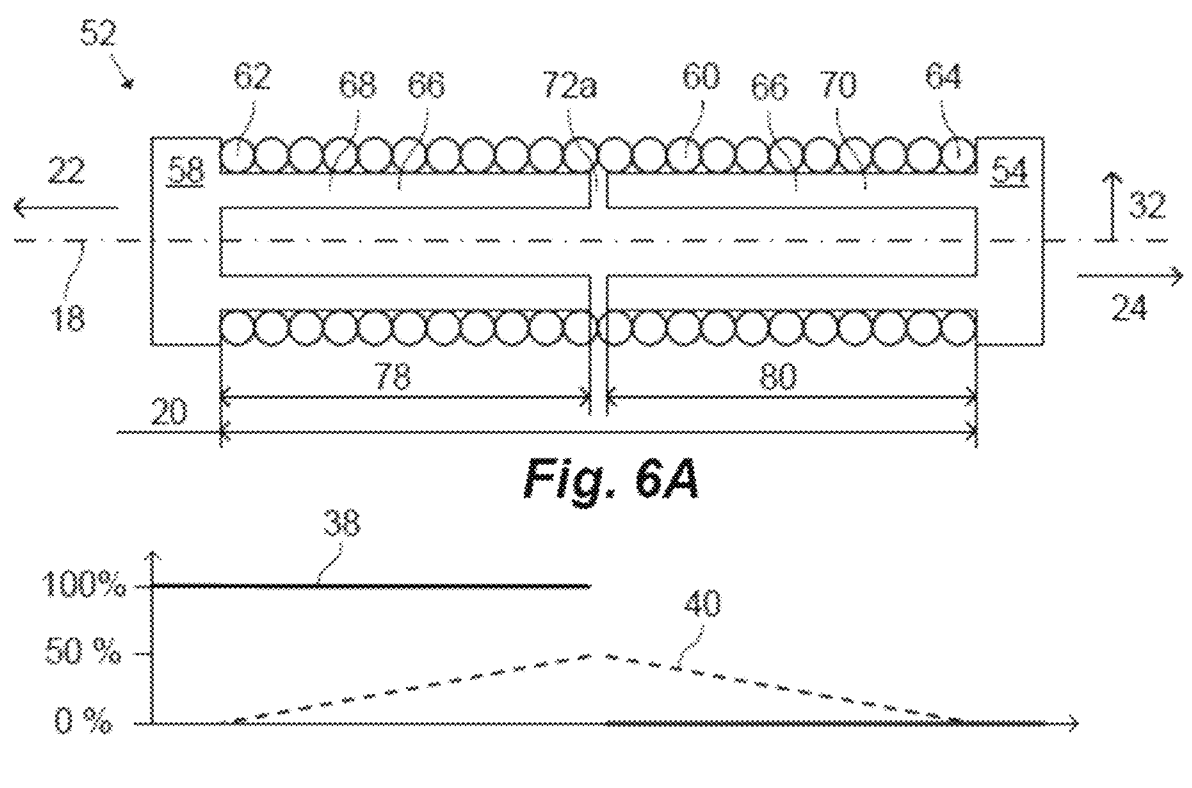
Fig. 6A
38
100%
40
50 %
0 %
Fig. 6B
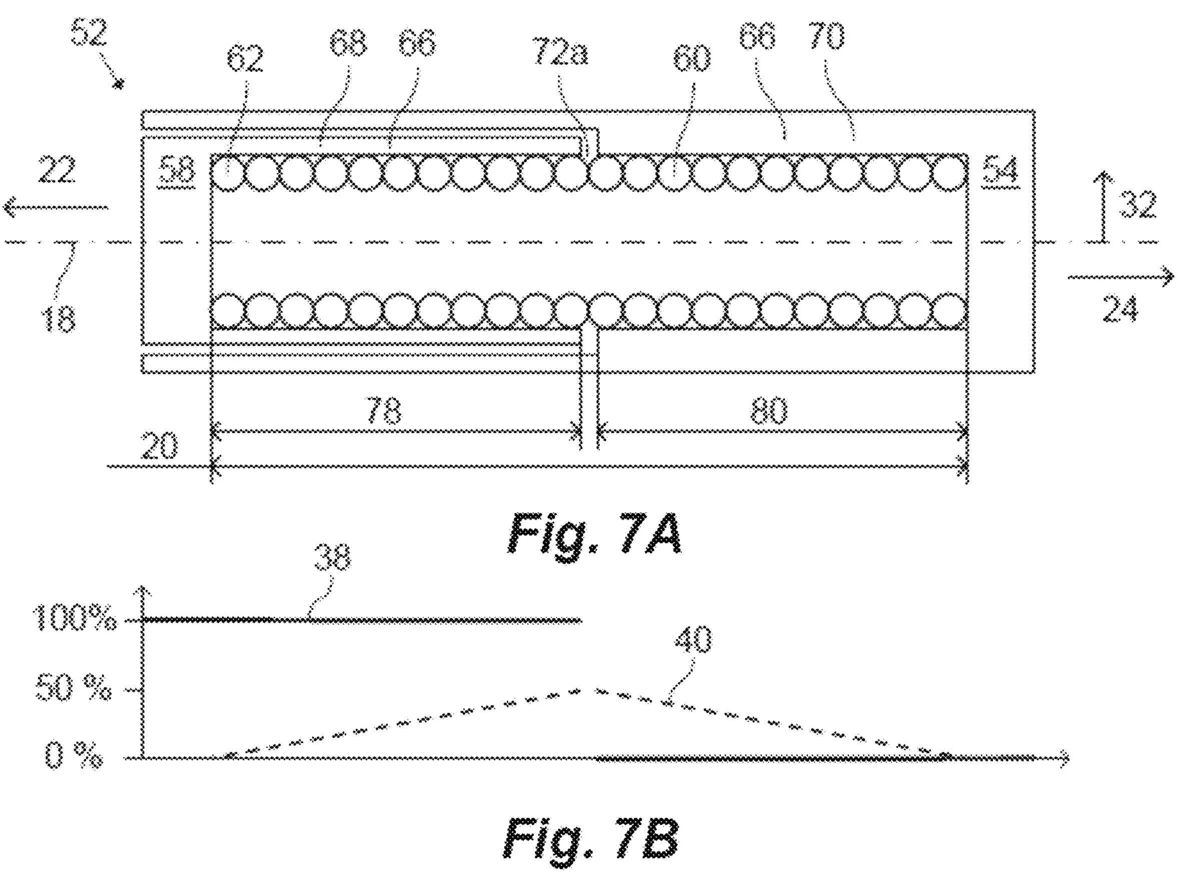
Fig. 7A
38
100%
40
50 %
0 %
Fig. 7B

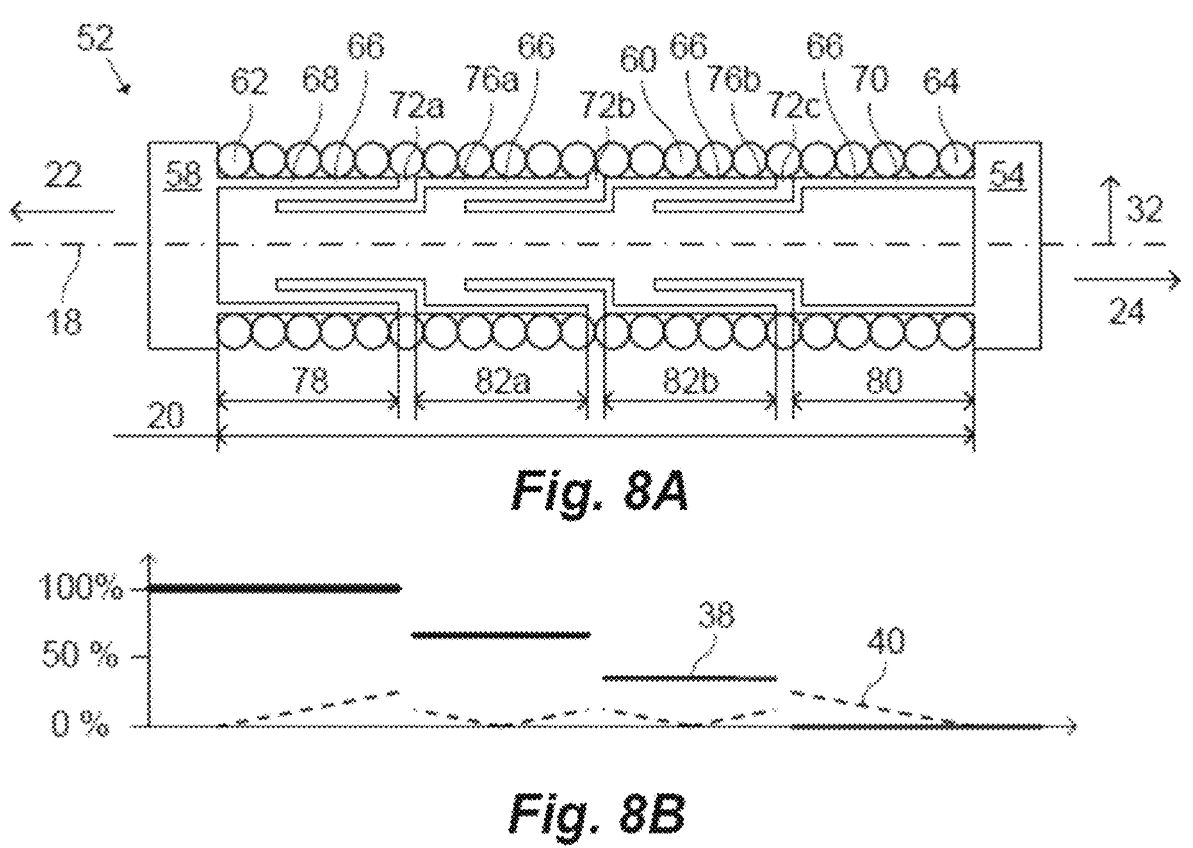
Fig. 8A
Fig. 8B
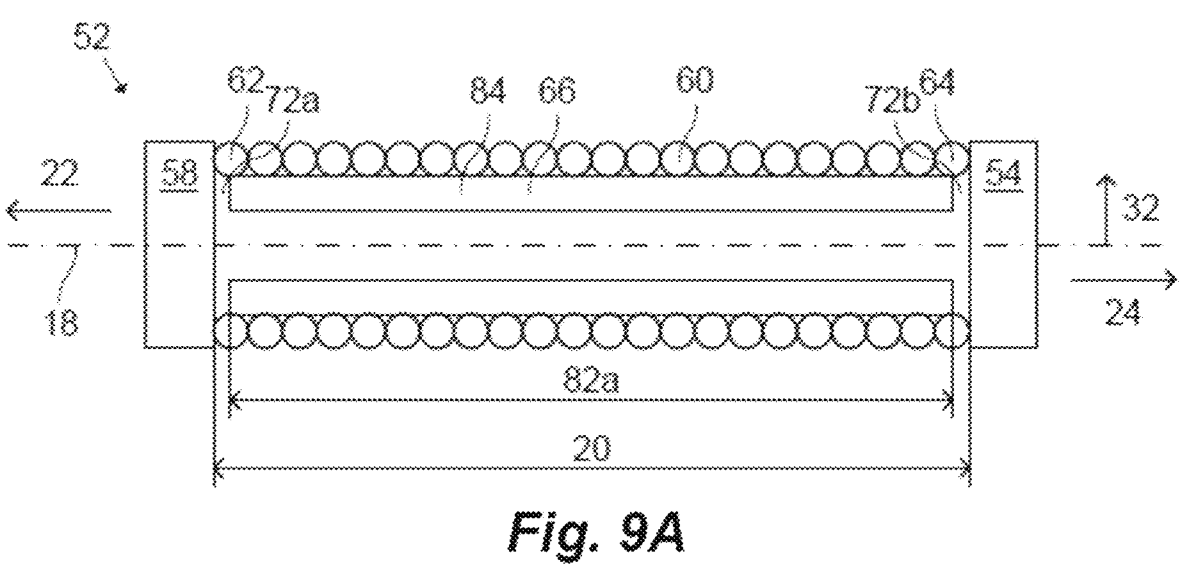
Fig. 9A
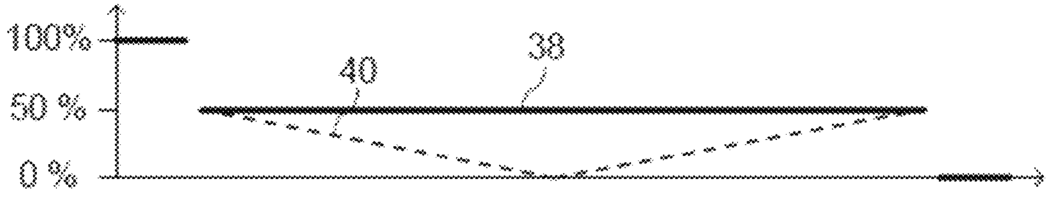
Fig. 9B

TORSION SPRING MECHANISM FOR MEDICAMENT DELIVERY DEVICE, AND MEDICAMENT DELIVERY DEVICE COMPRISING SAID MECHANISM

CROSS REFERENCE TO RELATED APPLICATIONS

The present application is a U.S. National Phase Application pursuant to 35 U.S.C. § 371 of International Application No. PCT/EP2021/081635 filed Nov. 15, 2021, which claims priority to European Patent Application No. 20208887.8 filed Nov. 20, 2020. The entire disclosure contents of these applications are herewith incorporated by reference into the present application.

TECHNICAL FIELD

The present disclosure generally relates to a mechanism for a medicament delivery device. In particular, a mechanism for a medicament delivery device, which mechanism comprises a torsion spring and at least one support part for laterally supporting the torsion spring, and a medicament delivery device comprising such mechanism, are provided.

BACKGROUND

Some medicament delivery devices, such as autoinjectors, are powered by mechanism comprising a torsion spring. The torsion spring may be a helical torsion spring with plurality of coils longitudinally aligned with one another, the torsion spring has one end connected to a base structure and one end connected to a driver. Upon release of the torsion spring in a deformed state, the torsion spring rotationally drives the driver relative to the base structure. This rotation of the driver may cause a plunger rod to be driven to expel medicament from a medicament container. In such mechanisms, the torsion spring tends to buckle significantly during operation. In order to avoid buckling, the mechanism may comprise a guide rod located inside the torsion spring or a guide tube located outside the torsion spring to limit the buckling of the torsion spring.

The guide rod may be a static component relative to the torsion spring; however, since the guide rod is configured to prevent the torsion spring from buckling, the inner or outer surface of the torsion spring will contact to the guide rod during operation. Because the guide rod is static, the contact between the guide rod and the inner or outer surface of the torsion spring generates friction and therefore causing a losing efficiency of the operation of the torsion spring.

SUMMARY

The present disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", "circumferentially", "radial", "radially", "rotation", "rotational" and "rotationally" refer to a direction generally perpendicular to the longitudinal direction and at least partially extending around the longitudinal direction.

According to one aspect, there is provided a mechanism for a medicament delivery device, the mechanism comprising a base structure; a plunger rod movable relative to the base structure along a longitudinal axis; a driver rotatable relative to the base structure about the longitudinal axis and engaging the plunger rod; a torsion spring having a rotatable end connected to the driver and a base end connected to the base structure, the torsion spring being arranged to rotationally drive the driver; and at least one support part arranged to support the torsion spring in a lateral direction with respect to the longitudinal axis; wherein the mechanism comprises at least one rotational interface between the driver and the base structure; and wherein the at least one rotational interface is positioned at between 0.5% and 99.5% of a length of the torsion spring along the longitudinal axis from the driver to the base structure; and/or wherein the at least one rotational interface comprises a first rotational interface positioned at less than 10% of the length of the torsion spring along the longitudinal axis from the driver to the base structure and a second rotational interface positioned at more than 90% of the length of the torsion spring along the longitudinal axis from the driver to the base structure.

The mechanism can therefore be more energy efficient; and can have low frictional losses.

When the driver rotates, the rotatable end rotates with the same speed as the driver. The base end may be stationary. A rotational speed of the torsion spring may then be substantially linearly increasing along the longitudinal axis from the base structure to the driver.

By means of the at least one rotational interface positioned at between 0.5% and 99.5% of the length of the torsion spring, or the first rotational interface positioned at 0% to 10% and the second rotational interface positioned at 90% to 100% of the length of the torsion spring, the mechanism provides a segmented support of the torsion spring where a maximum relative rotational speed between the torsion spring and the support part is substantially less than 100%. In this way, the mechanism significantly reduces friction losses in comparison with prior art solutions for laterally supporting a torsion spring.

Moreover, in some variants of the mechanism, the rotatable end is pivotally connected to the driver and the base end is pivotally connected to the base structure. The rotatable end may thereby pivot relative to the driver about an axis perpendicular to the longitudinal axis and the base end may thereby pivot relative to the base structure about an axis perpendicular to the longitudinal axis. Extra rubbing is thereby generated between the torsion spring and the at least one support part adjacent to the pivotal connections (e.g. at a point connects to a first coil and at a point connects to a last coil of the torsion spring). By providing the at least one rotational interface at between 10% and 90% of the length of the torsion spring, or the first rotational interface at 0% to 10% of the length of the torsion spring and the second rotational interface at 90% to 100% of the length of the torsion spring, the mechanism enables reduced local relative rotational speeds between the torsion spring and the at least one support part. The mechanism therefore enables the use of pivotal connections of the torsion spring to the driver and to the base structure, while still lowering frictional losses. The design of the mechanism can therefore be simple and cost effective. To provide such pivotal connections, the torsion spring may comprise a first hook engaging the driver and a second hook engaging the base structure.

Some variants of the mechanism have been further described as follows.

The at least one support part may form a guide rod for the torsion spring. In case the at least one support part comprises two support parts and a rotational interface positioned at 50% of the length of the torsion spring along the longitudinal axis from the driver to the base structure, the mechanism may be said to comprise a guide rod divided in half.

In case the at least one rotational interface comprises a first rotational interface at less than 10% of the length of the torsion spring and a second rotational interface at more than 90% of the length of the torsion spring, the at least one support part may comprise only one support part. The first rotational interface will then be provided between the driver and the single support part and the second rotational interface will then be provided between the single support part and the base structure. When the driver rotates at 100% speed, this single support part will then rotate at approximately 50% of the speed of the driver.

The at least one support part may comprise a plurality of support parts. For example, the at least one support part may comprise ten support parts each arranged to rotate at a unique speed. By increasing the number of support parts, relative rotational speeds between each support part and the torsion spring adjacent to the support part can be reduced. Frictional losses between the torsion spring and the support parts can thereby be lowered. However, a too high number of support parts may make assembly and/or production more cumbersome. According to one variant, the at least one support part comprises one to ten support parts. In case the at least one support part comprises a plurality of support parts, each support part may have a substantially equal, or equal, length along the longitudinal axis.

The base structure may for example be a part of a housing of the medicament delivery device. The base structure may be stationary during operation of the mechanism. The base structure may be substantially concentric with, or concentric with, the longitudinal axis.

The plunger rod may substantially concentric with, or concentric with, the longitudinal axis. The plunger rod may be arranged inside the driver with respect to the lateral direction.

The driver may be may substantially concentric with, or concentric with, the longitudinal axis. The driver may be arranged to drive the plunger rod in a proximal direction by rotation about the longitudinal axis.

The torsion spring may be may substantially concentric with, or concentric with, the longitudinal axis. The rotatable end may be a proximal end of the torsion spring. The base end of the torsion spring may be a distal end of the torsion spring.

The lateral direction may be a radial direction with respect to the longitudinal axis. As used herein, a rotational interface is an interface between two components rotating at different speeds. Each rotational interface may comprise a gap between the respective components.

The mechanism may further comprise an actuating element, such as a button. In this case, the torsion spring may be arranged to rotationally drive the driver upon actuation of the actuating element.

The torsion spring may be a helical torsion spring. The helical torsion spring may have a generally cylindrical shape.

The driver may threadingly engage the plunger rod. As a possible alternative, the driver may engage the plunger rod via a transmission comprising a cam profile and a cam follower arranged to follow the cam profile. The cam profile may be provided on the plunger rod and the cam follower may be provided on the driver, or vice versa.

The at least one support part may comprise a second part, and a first part rotatable about the longitudinal axis relative to the base structure and relative to the second part. In this case, the mechanism may comprise only one rotational interface between the first part and the second part.

The first part may be fixed to the driver. Alternatively, or in addition, the second part may be fixed to the base structure. In case the first part is fixed to the driver and the second part is fixed to the base structure, the mechanism may comprise only one rotational interface at 40% to 60%, such as at 50%, of the length of the torsion spring along the longitudinal axis from the driver to the base structure.

According to one example, the at least one support part comprises the first part and the second part, where the first part is rotatable relative to the driver and the second part is rotatable relative to the base structure. In this case, the mechanism comprises three rotational interfaces, i.e. between the driver and the first part, between the first part and the second part, and between the second part and the base structure.

A length of the first part along the longitudinal axis may differ less than 20% from a length of the second part along the longitudinal axis. The first part and the second part may thus have a substantially equal, or equal, length along the longitudinal axis.

The at least one support part may further comprise at least one intermediate part arranged between the first part and the second part. In this case, the at least one intermediate part may be rotatable about the longitudinal axis relative to each of the first part and the second part. Each intermediate part may be arranged to support the torsion spring in the lateral direction. In this case, the mechanism comprises at least two rotational interfaces, i.e. between the first part and the at least one intermediate part, and between the at least one intermediate part and the second part. One or more further rotational interfaces may optionally be provided, e.g. between the driver and the first part, between two of the at least one intermediate parts, and/or between the second part and the base structure.

A length of the at least one intermediate part along the longitudinal axis may differ less than 20% from each of a length of the first part along the longitudinal axis and a length of the second part along the longitudinal axis. The first part, each intermediate part and the second part may thus have a substantially equal, or equal, length along the longitudinal axis.

The at least one support part may be arranged inside the torsion spring with respect to the lateral direction. In this case, the at least one support part may constitute a segmented guide rod.

Alternatively, or in addition, the at least one support part may be arranged outside the torsion spring with respect to the lateral direction. In this case, the at least one support part may constitute a segmented guide tube. According to one example, the mechanism comprises both a segmented guide rod laterally inside the torsion spring and a segmented guide tube laterally outside the torsion spring.

Each of the at least one support part may be cylindrical. Alternatively, or in addition, each of the at least one support part may be substantially concentric with, or concentric with, the longitudinal axis.

The rotatable end may comprise a first leg connected to the driver and extending in the lateral direction. Alternatively, or in addition, the base end may comprise an over center second leg connected to the base structure. By means of the first leg and the second leg, buckling of the torsion spring can be reduced. As a consequence, frictional losses of the mechanism can be further reduced. The first leg may or may not be an over center leg.

The rotatable end may be fixed to the driver. Alternatively, or in addition, the base end may be fixed to the base structure. By fixing the rotatable end to the driver and the base end to the base structure, each of the rotatable end and the base end can transmit a pure moment to the torsion spring, and each of the rotatable end and the base end is prevented from pivoting about an axis perpendicular to the longitudinal axis. The extra rubbing between the torsion spring and the at least one support part due to pivoting is thereby avoided. As a consequence, frictional losses of the mechanism can be further reduced.

According to a further aspect, there is provided a medicament delivery device comprising a mechanism according to the present disclosure, and a medicament container. The plunger rod may be arranged to propel medicament out from the medicament container when being driven by rotation of the driver.

The medicament delivery device may further comprise a medicament delivery member. The medicament delivery member may for example be an injection needle or a nozzle.

BRIEF DESCRIPTION OF THE DRAWINGS

Further details, advantages and aspects of the present disclosure will become apparent from the following description taken in conjunction with the drawings, wherein:

FIG. 6A schematically represents a cross-sectional side view of the mechanism in FIGS. 1 to 3;

FIG. 6B schematically represents rotational speeds of a driver and the support parts, as well as relative rotational speeds between the torsion spring and the support parts in FIG. 6A;

FIG. 7A schematically represents a cross-sectional side view of the mechanism in FIG. 4;

FIG. 7B schematically represents rotational speeds of a driver and the support parts, as well as relative rotational speeds between the torsion spring and the support parts in FIG. 7A;

FIG. 8A schematically represents a cross-sectional side view of the mechanism in FIG. 5;

FIG. 8B schematically represents rotational speeds of a driver and the support parts, as well as relative rotational speeds between the torsion spring and the support parts in FIG. 8A;

FIG. 9A schematically represents a further example of a mechanism for a medicament delivery device comprising a torsion spring and a single support part;

FIG. 9B schematically represents rotational speeds of a driver and the support part, as well as relative rotational speeds between the torsion spring and the support part in FIG. 9A;

DETAILED DESCRIPTION

Figure 1:
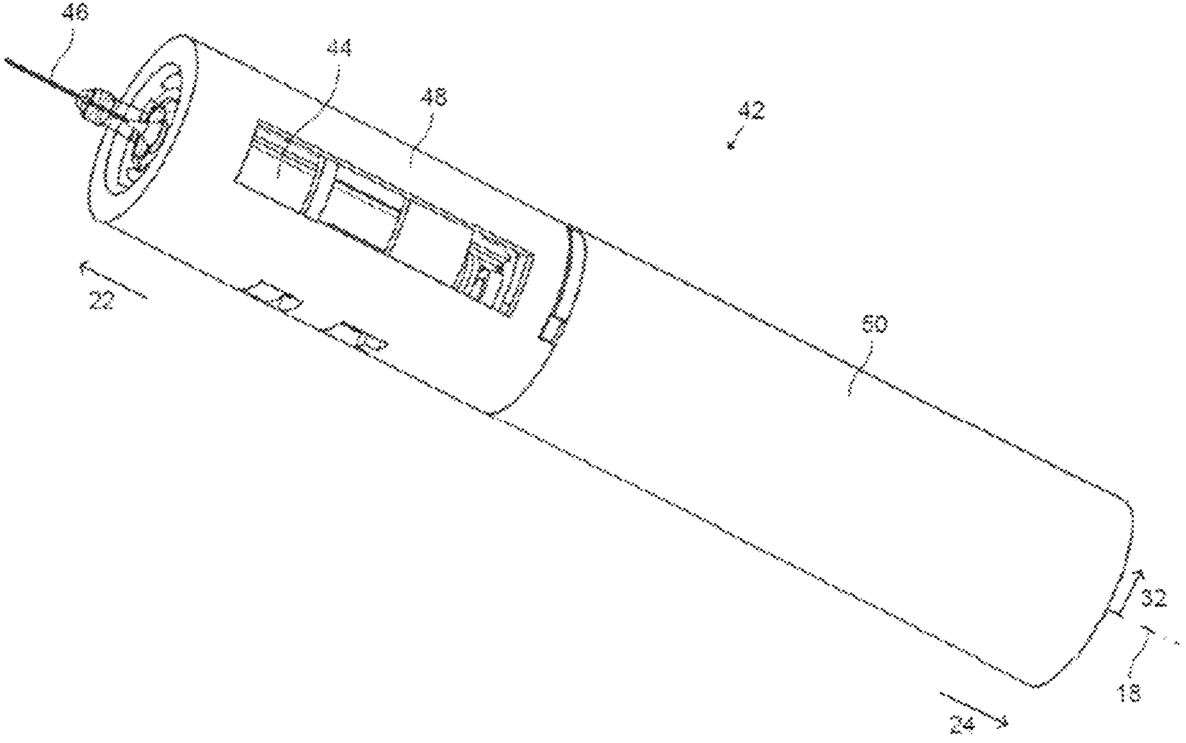
FIG. 1 schematically represents a perspective view of a medicament delivery device comprising a mechanism having a torsion spring and support parts.

In the following, a mechanism for a medicament delivery device, which mechanism comprises a torsion spring and at least one support part for laterally supporting the torsion spring, and a medicament delivery device comprising such mechanism, will be described. The same or similar reference numerals will be used to denote the same or similar structural features.

FIG. 1 schematically represents a perspective view of a medicament delivery device 42. FIG. 1 further shows a proximal direction 22 and a distal direction 24, opposite to the proximal direction 22. The medicament delivery device 42 comprises a medicament container 44. The medicament delivery device 42 of this specific example further comprises an injection needle 46, a proximal housing 48 and a distal housing 50.

The medicament delivery device 42 further comprises a longitudinal axis 18. FIG. 1 further shows a lateral direction 32 with respect to the longitudinal axis 18. The lateral direction 32 is perpendicular to the longitudinal axis 18. In this example, the lateral direction 32 is also a radial direction.

Figure 2:
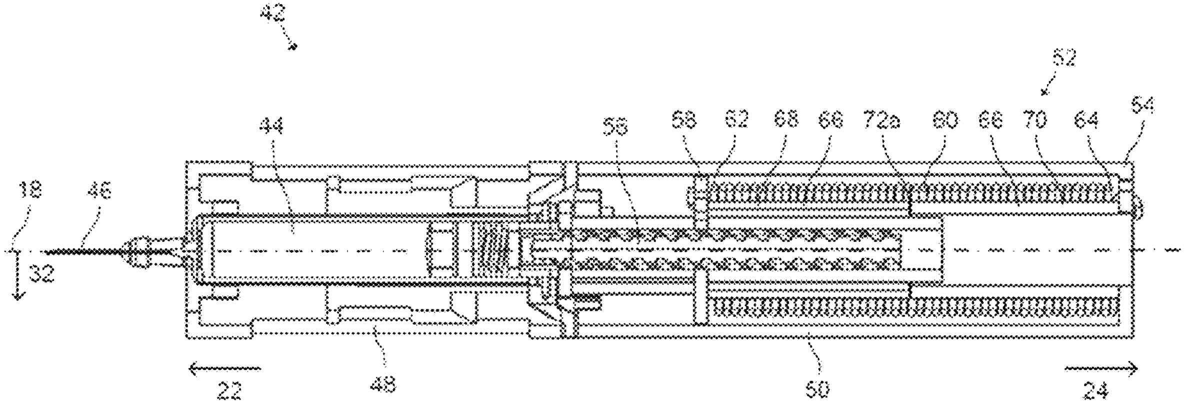
FIG. 2 schematically represents a cross-sectional side view of the medicament delivery device.

FIG. 2 schematically represents a cross-sectional side view of the medicament delivery device 42 in FIG. 1. The medicament delivery device 42 comprises a mechanism 52. The mechanism 52 comprises a base structure 54, a plunger rod 56, a driver 58 and a torsion spring 60.

The base structure 54 is here constituted by a distal part of the distal housing 50. The base structure 54 is concentric with the longitudinal axis 18.

The plunger rod 56 is movable along the longitudinal axis 18 in the proximal direction 22 relative to the base structure 54. In this way, medicament can be pushed out from the medicament container 44 and through the injection needle 46. The plunger rod 56 of this example comprises an external thread and passes through the driver 58. The plunger rod 56 is concentric with the longitudinal axis 18.

The driver 58 is rotatable relative to the base structure 54 about the longitudinal axis 18. The driver 58 engages the plunger rod 56. In this example, the driver 58 comprises an internal thread arranged to engage the external thread of the plunger rod 56. Due to the engagement between the driver 58 and the plunger rod 56, the driver 58 forces the plunger rod 56 to move in the proximal direction 22 when the driver 58 rotates about the longitudinal axis 18. The driver 58 is concentric with the longitudinal axis 18.

The torsion spring 60 of this example is a helically coiled torsion spring that is formed by multiple coils continuously aligned to one another in the longitudinal axis. The torsion spring 60 therefore has a generally cylindrical shape and is concentric with the longitudinal axis 18. The torsion spring 60 comprises a rotatable end 62 at a proximal end thereof and a base end 64 at a distal end thereof. The rotatable end 62 is connected to the driver 58. The base end 64 is connected to the base structure 54. The torsion spring 60 comprises a first leg and a second leg for connecting to the driver 58 and the base structure 54, an example for the first leg and the second leg will be provided later. The first leg and the second leg are respectively extending from a first coil of the torsion spring 60 and a last coil of the torsion spring 60. The first coil of the torsion spring 60 should be the coil that is closest to the driver 58, or the rotatable end 62 than another other coil of the torsion spring 60; the last coil of the torsion spring 60 should be the coil that is closest to the base 58, or the base end 64 than another other coil of the torsion spring 60.

FIG. 6A shows a length 20 of the torsion spring 60 along the longitudinal axis 18 between the driver 58 and the base structure 54. The length 20 of the torsion spring 60 should be defined by a length measured from a proximal end of the first coil of the torsion spring 60 to a distal end of the last coil of the torsion spring 60. If the first leg and the second leg of the torsion spring 60 extend further (in the distal direction or the proximal direction) than the first coil and the last coil of the torsion spring 60, a length of any further extending of the first leg and/or the second leg should not be counted as the length 20 of the torsion spring 60 in this present disclosure.

The mechanism 52 further comprises a plurality of support parts 66. The plurality of support parts 66 is configured to surround the torsion spring 60 or be position within the torsion spring 60. In this specific example, the mechanism 52 comprises two support parts 66, namely a first part 68 and a second part 70. Each support part 66 is arranged to support the torsion spring 60 in the lateral direction 32. Moreover, each support part 66 is cylindrical and concentric with the longitudinal axis 18.

In FIG. 2, the first part 68 is fixed to the driver 58 and the second part 70 is fixed to the base structure 54. The first part 68 is arranged to rotate about the longitudinal axis 18 relative to the second part 70. A rotational interface **72*a* is provided between the first part 68 and the second part 70. The rotational interface 72*a* is thereby also provided between the driver 58 and the base structure 54. As shown in FIG. 2, the rotational interface 72*a* is centered between the driver 58 and the base structure 54. That is, the first part 68 and the second part 70 are of equal length along the longitudinal axis 18, in this case, the rotational interface 72*a* is positioned at 50% of the length 20 of the torsion spring 60 along the longitudinal axis 18 from the driver 58 to the base structure 54. The portion of the torsion spring 60 that is close to the rotatable end 62 will comprise a more significant rotating speed; and the base end 64 of the torsion spring 60 will comprise a less significant rotating speed, or even be static as the base 58. In this case, when the first part 68 is rotated the friction between the first part and the portion of the torsion spring 60 that is close to the rotatable end 62 can be reduced; similarly, the second part 70 can be static as the base 58, or rotates with a slower speed than the first part 68, so that the friction between the second part and the portion of the torsion spring 60 that is close to the base end 64** can be also reduced.

In another example, the rotational interface **72*a* is positioned at any other percentage of the length 20 of the torsion spring 60 along the longitudinal axis 18 from the driver 58 to the base structure 54, only if the first coil of the torsion spring 60 being supported by the first part 68, namely, the rotational interface 72*a* should be positioned with a longitudinal distance to the driver 58 equal to at least half of the length of the first coil of the torsion spring 60 measured in the longitudinal direction. In a preferred example, the location of the rotational interface 72*a* relative to the length 20 of the torsion spring 60 along the longitudinal axis 18 from the driver 58 to the base structure 54, can be 0.5/total number of the coils (%) of the torsion spring 60, for example, if the torsion spring comprises 50 coils, then the rotational interface can be positioned at 1% (0.5/50%) of the length of the torsion spring along the longitudinal axis 18 from the driver 58 to the base structure 54. Because the first coil comprises a the most significant torque, so the most significant friction is usually generated between the first coil and the support parts; so that if there is no relative rotation or only slightly relative rotation between the first coil and the support parts, meaning the support parts that supports the first coil will be rotated together with the first coil, then the most significant friction can be reduced. In the example that the plurality supports 66 only comprises a first part 68 and a second part 70, meaning there will be only one rotational interface 72*a* positioned relative to the length 20 of the torsion spring 60 along the longitudinal axis 18 from the driver 58 to the base structure 54. In one example, the rotational interface 72*a* positioned at between 0.5% and 99.5% of the length 20 of the torsion spring 60, along the longitudinal axis 18 from the driver 58 to the base structure 54, namely the rotational interface 72*a* can be positioned at 0.5% or 10% or 12% or 15% or 30% or 45% or 65% of the length 20 of the torsion spring 60, along the longitudinal axis 18 from the driver 58 to the base structure 5; or any other positioned that is located between 0.5% and 99.5% of the length 20 of the torsion spring 60, along the longitudinal axis 18 from the driver 58 to the base structure 54**.

In a preferred embodiment, the rotational interface **72*a* positioned at between 0.5% and 75% of the length 20 of the torsion spring 60, along the longitudinal axis 18 from the driver 58 to the base structure 5. In a further preferred embodiment, the rotational interface 72*a* positioned at between 0.5% and 50% of the length 20 of the torsion spring 60, along the longitudinal axis 18 from the driver 58 to the base structure 5**.

It should be noted that, the rotational interface **72*a* can be formed on a contact point between the first part 68 and the second part 70, namely, the first part 68 is adjacent to the second part 70 at a point that defines the rotational interface 72*a*. However, the rotational interface 72*a* can be a gap between the first part 68 is adjacent to the second part 70. For supporting the torsion spring 60, a distance between the first part 68 and the second part 70, also namely the longitudinal length of the rotational interface 72*a* should be limited, e.g. being equal or less than a longitudinal length of three or two coils of the torsion spring 60**.

The first part 68 and the second part 70 are arranged inside the torsion spring 60 with respect to the lateral direction 32. The first part 68 and the second part 70 thereby form a segmented guide rod for the torsion spring 60.

The driver 58 and the first part 68 constitute a first segment and the second part 70 and the base structure 54 constitute a second segment. The first segment and the second segment are arranged to rotate at different speeds.

The medicament delivery device 42 can be prepared by rotationally deforming the torsion spring 60. To this end, the distal housing 50 may be manually rotated relative to the proximal housing 48 such that the torsion spring 60 is tensioned and is held tensioned. Upon activation of the medicament delivery device 42, e.g. by means of an activating element, the spring force in the torsion spring 60 is released causing the driver 58 to rotate about the longitudinal axis 18 and thereby drive the plunger rod 56 along the longitudinal axis 18. The torsion spring 60 is thus arranged to rotationally drive the driver 58.

Figure 3:
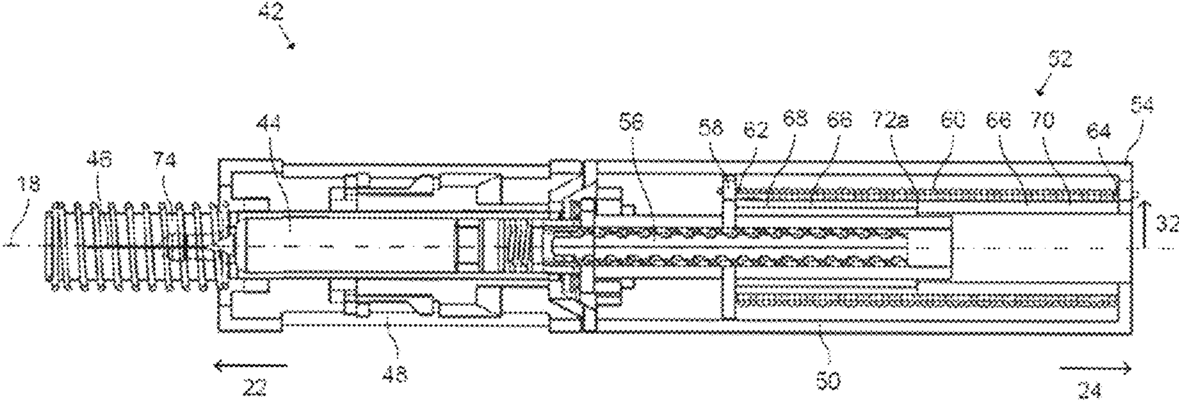
FIG. 3 schematically represents a cross-sectional side view of a further example of a medicament delivery device comprising a further example of a mechanism having a torsion spring and support parts.

FIG. 3 schematically represents a cross-sectional side view of a further example of a medicament delivery device 42 comprising a further example of a mechanism 52 having a torsion spring 60 and support parts 66. Mainly differences with respect to FIGS. 1 and 2 will be described. The medicament delivery device 42 in FIG. 3 comprises a cover 74 at a proximal end. The cover 74 covers the injection needle 46. The medicament delivery device 42 can be activated by pressing the cover 74 against an injection site. The mechanism 52 in FIG. 3 is of the same type as in FIGS. 1 and 2.

Figure 4:
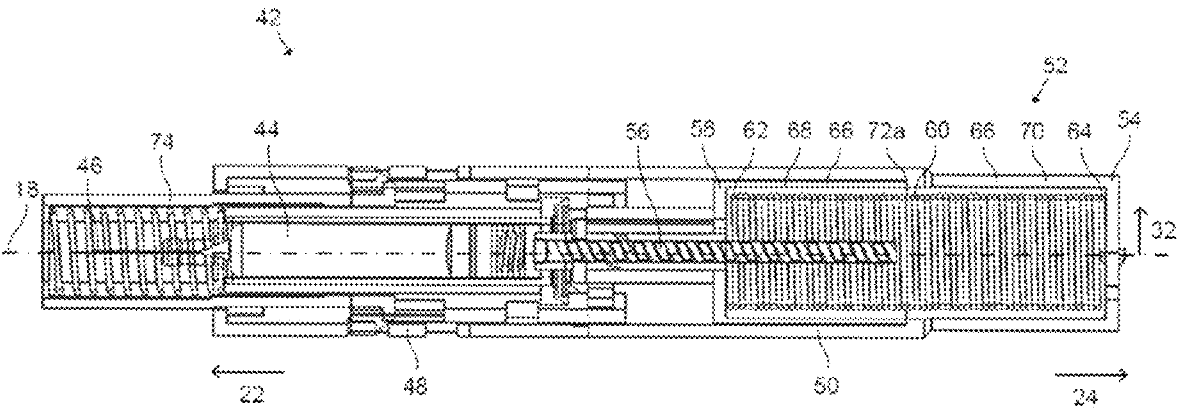
FIG. 4 schematically represents a cross-sectional side view of a further example of a medicament delivery device comprising a further example of a mechanism having a torsion spring and support parts.

FIG. 4 schematically represents a cross-sectional side view of a further example of a medicament delivery device 42 comprising a further example of a mechanism 52 having a torsion spring 60 and support parts 66. Mainly differences with respect to FIG. 3 will be described. In the mechanism 52 in FIG. 4, the first part 68 and the second part 70 is arranged outside the torsion spring 60 with respect to the lateral direction 32. The first part 68 and the second part 70 thereby form a segmented guide tube for the torsion spring 60.

Figure 5:
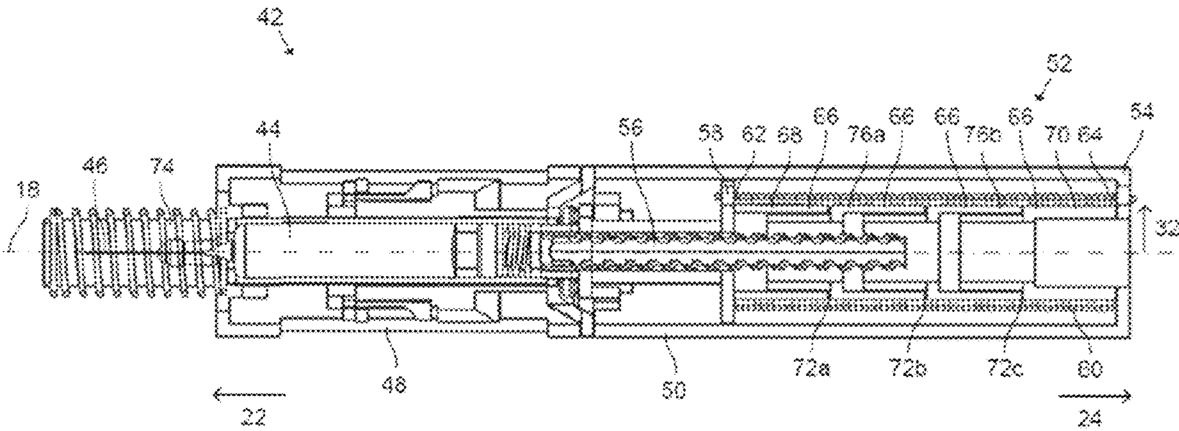
FIG. 5 schematically represents a cross-sectional side view of a further example of a medicament delivery device comprising a further example of a mechanism having a torsion spring and support parts.

FIG. 5 schematically represents a cross-sectional side view of a further example of a medicament delivery device 42 comprising a further example of a mechanism 52 having a torsion spring 60 and support parts 66. Mainly differences with respect to FIG. 3 will be described. The mechanism 52 in FIG. 5 comprises four support parts 66. In addition to the first part 68 and the second part 70, the four support parts 66 comprise a first intermediate part **76*a* and a second intermediate part 76*b*. Each of the first intermediate part 76*a* and the second intermediate part 76*b* is arranged to support the torsion spring 60 in the lateral direction 32**.

Similar to the mechanism 52 in FIGS. 2 to 4, the first part 68 is fixed to the driver 58 and the second part 70 is fixed to the base structure 54. The first intermediate part **76*a* is arranged between the first part 68 and the second intermediate part 76*b*. The second intermediate part 76*b* is arranged between the first intermediate part 76*a* and the second part 70. Each of the first intermediate part 76*a* and the second intermediate part 76*b* is arranged to rotate independently about the longitudinal axis 18**.

The mechanism 52 in FIG. 5 comprises a first rotational interface **72*a* between the first part 68 and the first intermediate part 76*a*, a second rotational interface 72*b* between the first intermediate part 76*a* and the second intermediate part 76*b*, and a third rotational interface 72*c* between the second intermediate part 76*b* and the second part 70. Each of the first rotational interface 72*a*, the second rotational interface 72*b* and the third rotational interface 72*c* is arranged between the driver 58 and the base structure 54. The first rotational interface 72*a*, the second rotational interface 72*b* and the third rotational interface 72*c* are positioned at 25%, 50% and 75%, respectively, of a length of the torsion spring 60 along the longitudinal axis 18 from the driver 58 to the base structure 54. Thus, each support part 66 has the same length along the longitudinal axis 18**.

Similarly, the first and the second rotational interface **72*a*, 72*b* can be formed on contact points between the first part 68 and the first intermediate part 76*a*, and the third rotational interface 72*c* between the second intermediate part 76*b* and the second part 70. Alternative, the first and the second rotational interface 72*a*, 72*b* can be a gap between the first part 68 and the first intermediate part 76*a*, and a third rotational interface 72*c* between the second intermediate part 76*b* and the second part 70. For supporting the torsion spring 60, a distance between the between the first part 68 and the first intermediate part 76*a*, and a third rotational interface 72*c* between the second intermediate part 76*b* and the second part 70, also namely the longitudinal length of the first and the second rotational interface 72*a*, 72*b* should be limited, e.g. being equal or less than a longitudinal length of three or two coils of the torsion spring 60**.

FIG. 6A schematically represents a cross-sectional side view of the mechanism 52 in FIGS. 1 to 3, and FIG. 6B schematically represents rotational speeds 38 of the driver 58 and the support parts 66, as well as relative rotational speeds 40 between the torsion spring 60 and the support parts 66 in FIG. 6A.

A length 78 of the first part 68 along the longitudinal axis 18, and a length 80 of the second part 70 along the longitudinal axis 18. As shown in FIG. 6B, the rotational speed 38 of the driver 58 and the first part 68 is 100% and the rotational speed 38 of the second part 70 and the base structure 54 is 0% during operation of the mechanism 52.

The rotational speed of the torsion spring 60 is substantially linearly increasing in the proximal direction 22 along the longitudinal axis 18 from 0% adjacent to the base structure 54 to 100% adjacent to the driver 58. On average, the rotational speed of the torsion spring 60 is 50% of the rotational speed of the driver 58. A center of the torsion spring 60 along the longitudinal axis 18 also rotates at approximately 50% of the rotational speed of the driver 58. The proximal half of the torsion spring 60 rotates at 75% of the rotational speed of the driver 58 on average. Since the first part 68 rotates at 100% of the rotational speed of the driver 58, the maximum relative rotational speed 40 between the torsion spring 60 and the first part 68 is 50%.

The distal half of the torsion spring 60 rotates at 25% of the rotational speed of the driver 58 on average. Since the second part 70 is stationary, the maximum relative rotational speed 40 between the torsion spring 60 and the second part 70 is 50%. Since the maximum relative rotational speed 40 between the torsion spring 60 and any of the support parts 66 is approximately 50% in this example, frictional losses are substantially reduced. The segmented support parts 66 in FIG. 6A thereby generate only half as much friction as a static guide rod.

FIG. 7A schematically represents a cross-sectional side view of the mechanism 52 in FIG. 4, and FIG. 7B schematically represents rotational speeds 38 of the driver 58 and the support parts 66, as well as relative rotational speeds 40 between the torsion spring 60 and the support parts 66 in FIG. 7A. Also with the arrangement of the support parts 66 according to FIGS. 4 and 7A, the maximum relative rotational speed 40 between the torsion spring 60 and any of the support parts 66 is approximately 50%. Frictional losses are therefore substantially reduced.

FIG. 8A schematically represents a cross-sectional side view of the mechanism 52 in FIG. 5, and FIG. 8B schematically represents rotational speeds 38 of the driver 58 and the support parts 66, as well as relative rotational speeds 40 between the torsion spring 60 and the support parts 66 in FIG. 8A. FIG. 8A further shows a length 82*a* of the first intermediate part 76*a* along the longitudinal axis 18 and a length 82*b* of the second intermediate part 76*b* along the longitudinal axis 18.

As shown in FIG. 8B, the rotational speeds 38 of the first intermediate part 76*a* and the second intermediate part 76*b* are approximately 67% and 33%, respectively, of the rotational speed 38 of the driver 58. By increasing the number of support parts 66, the relative rotational speeds 40 between each support part 66 and the torsion spring 60 can be further reduced. As shown in FIG. 8*b*, the maximum relative rotational speed 40 between the first part 68 and the torsion spring 60 is approximately 25%, the maximum relative rotational speed 40 between the first intermediate part 76*a* and the torsion spring 60 is approximately 12.5%, the maximum relative rotational speed 40 between the second intermediate part 76*b* and the torsion spring 60 is approximately 12.5%, and the maximum relative rotational speed 40 between the second part 70 and the torsion spring 60 is approximately 25%.

FIG. 9A schematically represents a further example of a mechanism 52 for a medicament delivery device 42 comprising a torsion spring 60. In FIG. 9A, the at least one support part 66 is constituted by a single support part 84. The mechanism 52 comprises a first rotational interface 72*a* between the driver 58 and the single support part 84 and a second rotational interface 72*b* between the single support part 84 and the base structure 54. The first rotational interface 72*a* is positioned at 0% of the length 20 of the torsion spring 60 along the longitudinal axis 18 from the driver 58 to the base structure 54. The second rotational interface 72*b* is positioned at 100% of the length 20 of the torsion spring 60 along the longitudinal axis 18 from the driver 58 to the base structure 54.

FIG. 9B schematically represents rotational speeds 38 of the driver 58 and the single support part 84, as well as relative rotational speeds 40 between the torsion spring 60 and the single support part 84 in FIG. 9A. When the driver 58 rotates at 100% speed, the rotational speed 38 of the single support part 84 is approximately 50% of the rotational speed 38 of the driver 58. As shown in FIG. 9B, the maximum relative rotational speed 40 between the single support part 84 and the torsion spring 60 is approximately 50%. Thus, also by means of the mechanism 52 in FIG. 9A, frictional losses can be substantially reduced.

Figure 10A:
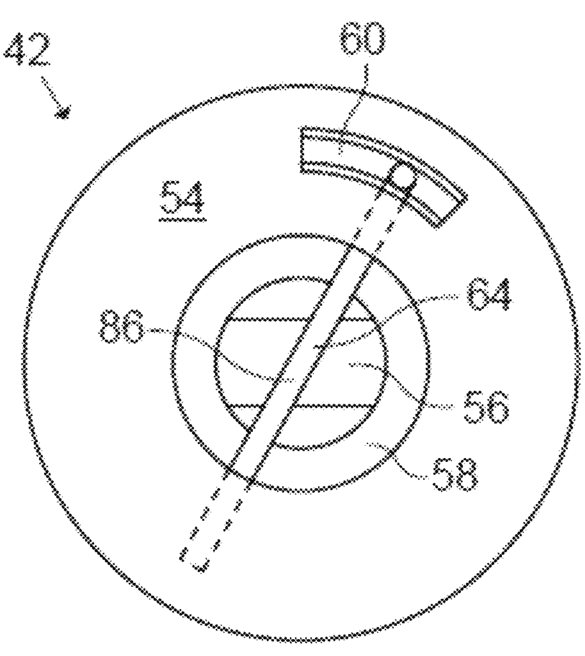
FIG. 10A schematically represents a view of a further example of a medicament delivery device in a proximal direction.
Figure 10B:
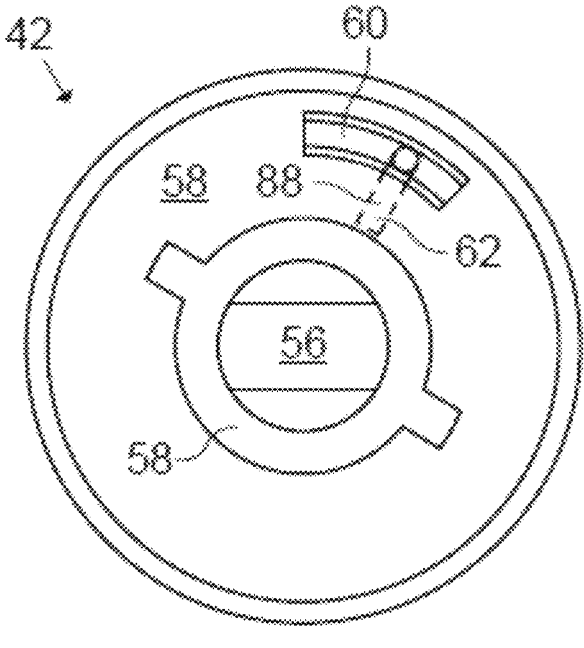
FIG. 10B schematically represents a cross-sectional view of the medicament delivery device in FIG. 10A in a distal direction.

FIG. 10A schematically represents a view of a further example of a medicament delivery device 42 in the proximal direction 22, and FIG. 10B schematically represents a cross-sectional view of the medicament delivery device 42 in FIG. 10A in the distal direction 24. With reference to FIGS. 10A and 10B, mainly differences with respect to the medicament delivery device 42 in FIGS. 1 and 2 will be described. As shown in FIG. 10A, the base end 64 of the torsion spring 60 comprises the second leg, in this example, the second leg is an over center second leg 86. The second leg 86 is straight and extends in the lateral direction 32 across the longitudinal axis 18. As shown in FIG. 10B, the rotatable end 62 of the torsion spring 60 comprises the first leg 88. The first leg 88 is straight and extends in the lateral direction 32 towards the longitudinal axis 18. By means of the first leg 88 and the second leg 86 each extending transverse to the longitudinal axis 18, buckling of the torsion spring 60 can be reduced. Consequently, frictional losses between the torsion spring 60 and the at least one support part 66 can be further reduced.

Moreover, the second leg 86 is fixed to the base structure 54 and the first leg 88 is fixed to the driver 58. Each of the base end 64 and the rotatable end 62 can thereby provide its own force couple. In this way, rubbing between a proximal coil of the torsion spring 60 and an adjacent support part 66, and rubbing between a distal coil of the torsion spring 60 and an adjacent support part 66, due to pivoting can thereby be avoided. In this way, frictional losses between the torsion spring 60 and the at least one support part 66 can be further reduced.

While the present disclosure has been described with reference to exemplary embodiments, it will be appreciated that the present disclosure is not limited to what has been described above. For example, it will be appreciated that the dimensions of the parts may be varied as needed. Accordingly, it is intended that the present disclosure may be limited only by the scope of the claims appended hereto.

The invention claimed is:

1. A mechanism for a medicament delivery device, the mechanism comprising:
- a base structure;
- a plunger rod movable relative to the base structure along a longitudinal axis;
- a driver rotatable relative to the base structure about the longitudinal axis and engaging the plunger rod;
- a torsion spring having a rotatable end connected to the driver and a base end connected to the base structure, the torsion spring being arranged to rotationally drive the driver; and
- at least one support part arranged to support the torsion spring in a lateral direction with respect to the longitudinal axis, wherein the at least one support part comprises a second part, and a first part rotatable about the longitudinal axis relative to the base structure and relative to the second part,
- wherein the mechanism comprises at least one rotational interface between the driver and the base structure, and
- wherein the at least one rotational interface is positioned at between 0.5% and 99.5% of a length of the torsion spring along the longitudinal axis from the driver to the base structure.

2. The mechanism according to claim 1, wherein the torsion spring is a helical torsion spring.

3. The mechanism according to claim 1, wherein the driver threadingly engages the plunger rod.

4. The mechanism according to claim 1, wherein the at least one rotational interface comprises a first rotational interface positioned at less than 10% of the length of the torsion spring along the longitudinal axis from the driver to the base structure and a second rotational interface positioned at more than 90% of the length of the torsion spring along the longitudinal axis from the driver to the base structure.

5. The mechanism according to claim 1, wherein the first part is fixed to the driver.

6. The mechanism according to claim 1, wherein the second part is fixed to the base structure.

7. The mechanism according to claim 1, wherein a length of the first part along the longitudinal axis differs less than 20% from a length of the second part along the longitudinal axis.

8. The mechanism according to claim 1, wherein the at least one support part further comprises at least one intermediate part arranged between the first part and the second part, the at least one intermediate part being rotatable about the longitudinal axis relative to each of the first part and the second part.

9. The mechanism according to claim 8, wherein a length of the at least one intermediate part along the longitudinal axis differs less than 20% from each of a length of the first part along the longitudinal axis and a length of the second part along the longitudinal axis.

10. The mechanism according to claim 1, wherein the at least one support part is arranged inside the torsion spring with respect to the lateral direction.

11. The mechanism according to claim 1, wherein each of the at least one support part is cylindrical.

12. The mechanism according to claim 1, wherein each of the at least one support part is concentric with the longitudinal axis.

13. The mechanism according to claim 1, wherein the rotatable end comprises a first leg connected to the driver and extending in the lateral direction, and/or wherein the base end comprises an over center second leg connected to the base structure.

14. The mechanism according to claim 1, wherein the rotatable end is fixed to the driver and/or wherein the base end is fixed to the base structure.

15. A medicament delivery device comprising the mechanism according to claim 1, and a medicament container.

16. A mechanism for a medicament delivery device, the mechanism comprising:

a base structure;

a plunger rod movable relative to the base structure along a longitudinal axis;

a driver rotatable relative to the base structure about the longitudinal axis while engaging the plunger rod;

a torsion spring arranged around a support part, where the torsion spring comprises a rotatable end connected to the driver and a base end connected to the base structure, where a release of tension of the torsion spring rotates the driver, wherein the support part comprises a first part and a second part, where the first part is fixed to the driver and rotates about the longitudinal axis relative to both the base structure and the second part that is fixed to base structure; and a rotational interface located between the driver and the base structure, where the rotational interface is positioned at between 0.5% and 99.5% of a length of the torsion spring along the longitudinal axis from the driver to the base structure.

17. The mechanism according to claim 16, wherein the at rotational interface comprises a first rotational interface positioned at less than 10% of the length of the torsion spring along the longitudinal axis from the driver to the base structure and a second rotational interface positioned at more than 90% of the length of the torsion spring along the longitudinal axis from the driver to the base structure.

18. The mechanism according to claim 16, wherein a length of the first part along the longitudinal axis differs less than 20% from a length of the second part along the longitudinal axis.

19. The mechanism according to claim 18, wherein the support part further comprises an intermediate part arranged between the first part and the second part, the intermediate part rotates about the longitudinal axis relative to both the first part and the second part.

20. The mechanism according to claim 16, wherein the support part is concentric with the longitudinal axis.

* * * * *